United States Patent
Kitamura et al.

(10) Patent No.: US 12,419,491 B2
(45) Date of Patent: Sep. 23, 2025

(54) ENDOSCOPE DIAGNOSIS SUPPORT SYSTEM, STORAGE MEDIUM, AND ENDOSCOPE DIAGNOSIS SUPPORT METHOD

(71) Applicant: OLYMPUS CORPORATION, Tokyo (JP)

(72) Inventors: Makoto Kitamura, Hachioji (JP); Katsuyoshi Taniguchi, Hino (JP); Hirokazu Godo, Hachioji (JP); Takashi Kono, Hachioji (JP); Toshiya Kamiyama, Tama (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 317 days.

(21) Appl. No.: 16/665,040

(22) Filed: Oct. 28, 2019

(65) Prior Publication Data
US 2020/0126223 A1    Apr. 23, 2020

Related U.S. Application Data

(63) Continuation of application No. PCT/JP2017/016961, filed on Apr. 28, 2017.

(51) Int. Cl.
*A61B 1/00*    (2006.01)
*A61B 1/06*    (2006.01)
*G06T 7/00*    (2017.01)

(52) U.S. Cl.
CPC .. *A61B 1/000094* (2022.02); *A61B 1/000096* (2022.02); *A61B 1/00045* (2013.01);
(Continued)

(58) Field of Classification Search
CPC .......... G02B 23/24; G06T 2207/10068; G06T 2207/30204; G06T 7/0012;
(Continued)

(56) References Cited

U.S. PATENT DOCUMENTS 6,167,296 A * 12/2000 Shahidi .................... A61B 5/06
600/117
6,371,908 B1* 4/2002 Furusawa ............ A61B 5/0059
600/160
(Continued)

FOREIGN PATENT DOCUMENTS

CN        101005794 A        7/2007
CN        101116608 A        2/2008
(Continued)

OTHER PUBLICATIONS

International Search Report dated Jul. 18, 2017 received in PCT/JP2017/016961.

*Primary Examiner* — Gandhi Thirugnanam
(74) *Attorney, Agent, or Firm* — Scully, Scott, Murphy & Presser, P.C.

(57) ABSTRACT

An endoscope diagnosis support system includes a processor. The processor performs detection of an anomaly candidate area from an endoscope image obtained by performing image pickup of an inside of a subject to obtain a detection result, and generates a display image in which an indicator indicating detection of the anomaly candidate area is arranged in a periphery portion of the endoscope image in accordance with the detection result.

32 Claims, 11 Drawing Sheets

(52) U.S. Cl.
CPC .......... *A61B 1/0655* (2022.02); *G06T 7/0012* (2013.01); *G06T 2207/10068* (2013.01); *G06T 2207/30096* (2013.01); *G06T 2207/30204* (2013.01)

(58) Field of Classification Search
CPC ........ H04N 2005/2255; A61B 1/00009; A61B 1/00045; A61B 1/0005; A61B 1/045; A61B 1/05; A61B 1/0676
See application file for complete search history.

(56) References Cited

U.S. PATENT DOCUMENTS

| | | | | |
|---|---|---|---|---|
| 9,697,541 | B1* | 7/2017 | Daniel | G06F 16/9554 |
| 2003/0078477 | A1* | 4/2003 | Kang | A61B 1/042 |
| | | | | 600/178 |
| 2006/0173358 | A1* | 8/2006 | Xie | A61B 1/0005 |
| | | | | 600/476 |
| 2006/0280347 | A1* | 12/2006 | Shirahata | A61B 6/00 |
| | | | | 382/128 |
| 2007/0078335 | A1* | 4/2007 | Horn | A61B 1/041 |
| | | | | 600/425 |
| 2008/0024599 | A1* | 1/2008 | Hirakawa | H04N 7/183 |
| | | | | 348/65 |
| 2009/0074270 | A1* | 3/2009 | Tanaka | G06T 7/74 |
| | | | | 382/128 |
| 2009/0131746 | A1* | 5/2009 | Seo | G16H 30/20 |
| | | | | 600/101 |
| 2010/0225209 | A1* | 9/2010 | Goldberg | A61B 34/37 |
| | | | | 312/209 |
| 2012/0026308 | A1* | 2/2012 | Johnson | H04N 7/18 |
| | | | | 348/E7.085 |
| 2012/0140989 | A1* | 6/2012 | Hori | G06T 7/136 |
| | | | | 382/106 |
| 2012/0274754 | A1* | 11/2012 | Tsuruoka | A61B 1/00045 |
| | | | | 348/65 |
| 2012/0321161 | A1* | 12/2012 | Ishikawa | G06T 19/00 |
| | | | | 345/419 |
| 2014/0296718 | A1* | 10/2014 | Kishima | A61B 5/0071 |
| | | | | 600/476 |
| 2014/0354442 | A1* | 12/2014 | Maity | G08B 27/005 |
| | | | | 340/691.6 |
| 2015/0078615 | A1* | 3/2015 | Staples, II | G06T 7/50 |
| | | | | 382/103 |
| 2016/0073927 | A1* | 3/2016 | Akimoto | A61B 1/00194 |
| | | | | 600/109 |
| 2016/0133014 | A1* | 5/2016 | Staples, II | A61B 1/0005 |
| | | | | 382/103 |
| 2016/0196643 | A1* | 7/2016 | Bendall | G06T 7/62 |
| | | | | 382/108 |
| 2017/0112357 | A1* | 4/2017 | Kono | A61B 1/3137 |
| 2017/0367559 | A1* | 12/2017 | Takahashi | A61B 1/00055 |
| 2018/0098690 | A1* | 4/2018 | Iwaki | G02B 23/2407 |
| 2018/0225820 | A1* | 8/2018 | Liang | G06V 10/82 |
| 2018/0249900 | A1 | 9/2018 | Imaizumi et al. | |
| 2019/0231444 | A1* | 8/2019 | Tojo | A61B 34/20 |
| 2019/0385018 | A1* | 12/2019 | Ngo Dinh | A61B 1/2736 |
| 2020/0126223 | A1* | 4/2020 | Kitamura | A61B 1/00009 |
| 2021/0000327 | A1* | 1/2021 | Kitamura | H04N 7/183 |
| 2021/0357109 | A1* | 11/2021 | Chang | G06F 3/0481 |

FOREIGN PATENT DOCUMENTS

| | | | | |
|---|---|---|---|---|
| CN | 108348145 A | | 7/2018 | |
| EP | 2517614 A1 | * | 10/2012 | ......... A61B 1/00009 |
| JP | 2004159739 A | | 6/2004 | |
| JP | 2010-172673 A | | 8/2010 | |
| JP | 2011-160848 A | | 8/2011 | |
| JP | 2011-255006 A | | 12/2011 | |
| WO | 2011/096279 A1 | | 8/2011 | |
| WO | 2017/073337 A1 | | 5/2017 | |
| WO | 2017/073338 A1 | | 5/2017 | |
| WO | WO-2018198327 A1 | * | 11/2018 | .......... A61B 1/0676 |
| WO | WO-2018230074 A1 | * | 12/2018 | |

* cited by examiner

ENDOSCOPE DIAGNOSIS SUPPORT SYSTEM, STORAGE MEDIUM, AND ENDOSCOPE DIAGNOSIS SUPPORT METHOD

CROSS REFERENCE TO RELATED APPLICATION

This application is a continuation application of PCT/JP2017/016961 filed on Apr. 28, 2017, the entire contents of which are incorporated herein by this reference.

BACKGROUND OF THE INVENTION

1. Field of the Invention

The present invention relates to an endoscope diagnosis support system, a storage medium, and an endoscope diagnosis support method.

2. Description of the Related Art

Up to now, a technology has been proposed in which image processing on a medical image is performed, and the medical image is displayed with a mark added to a part that matches a previously specified condition. For example, Japanese Patent Application Laid-Open Publication No. 2004-159739 discloses an image processing apparatus that performs image processing on a medical image obtained by an X-ray CT apparatus, a magnetic resonance photographing apparatus, an ultrasound diagnosis apparatus, an X-ray photographing apparatus, or the like, and adds a mark to a part that is suspected to be a lesion to be displayed such that diagnosis support can be performed.

SUMMARY OF THE INVENTION

An endoscope diagnosis support system according to an embodiment includes a processor. The processor performs detection of an anomaly candidate area from an endoscope image obtained by performing image pickup of an inside of a subject to obtain a detection result, and generates a display image in which an indicator indicating detection of the anomaly candidate area is arranged in a periphery portion of the endoscope image in accordance with the detection result.

A non-transitory storage medium according to an embodiment stores a computer-readable program. The program causes a computer to execute code for performing detection of an anomaly candidate area from an endoscope image obtained by performing image pickup of an inside of a subject to obtain a detection result, and code for generating a display image in which an indicator indicating detection of the anomaly candidate area is arranged in a periphery portion of the endoscope image in accordance with the detection result.

An endoscope diagnosis support method according to an embodiment includes performing detection of an anomaly candidate area from an endoscope image obtained by performing image pickup of an inside of a subject to obtain a detection result, and generating a display image in which an indicator indicating detection of the anomaly candidate area is arranged in a periphery portion of the endoscope image in accordance with the detection result.

DETAILED DESCRIPTION OF THE PREFERRED EMBODIMENTS

Hereinafter, embodiments of the present invention are described with reference to the drawings.

First Embodiment (Configuration)

Figure 1:
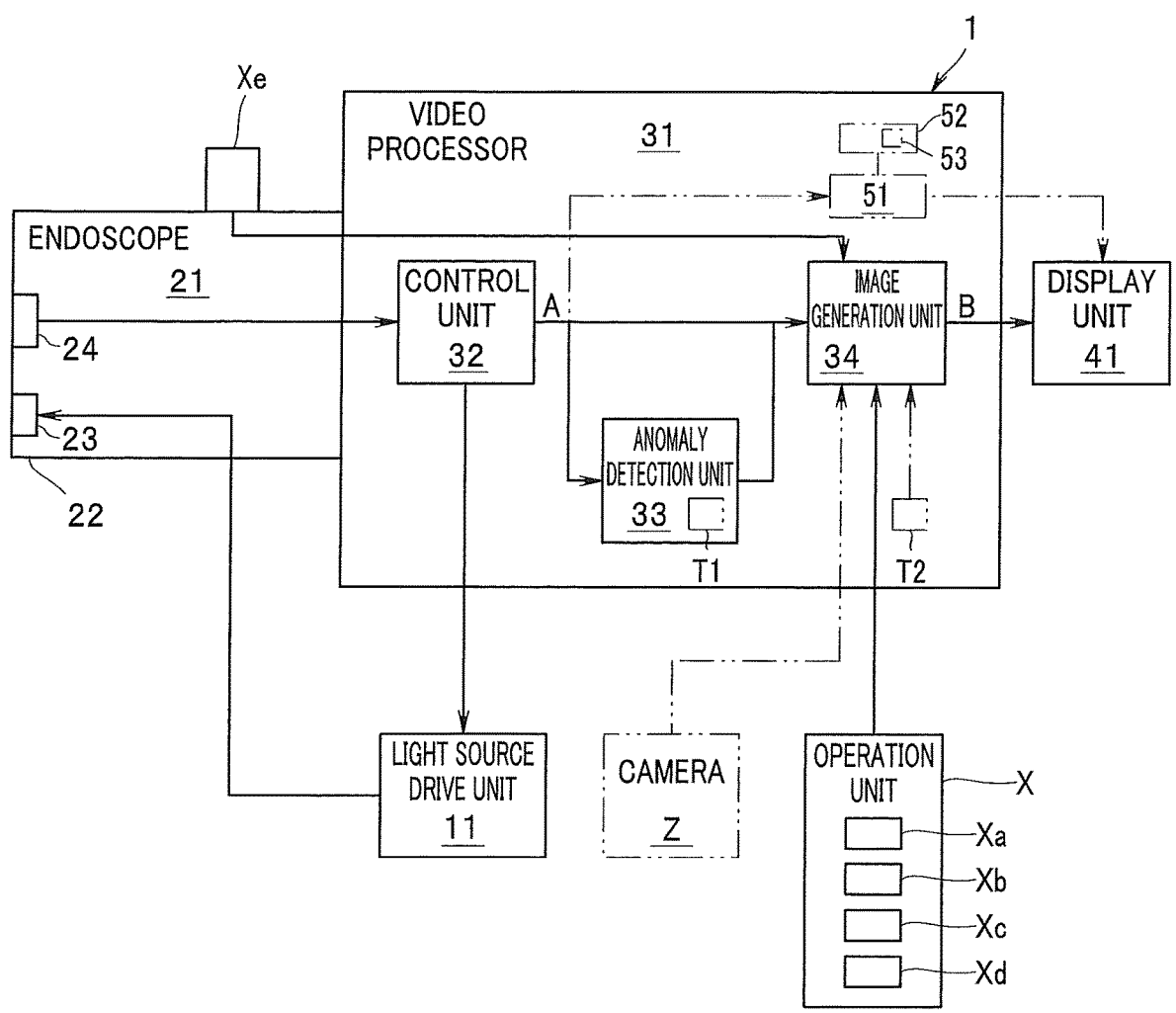
FIG. 1 is a block diagram illustrating a configuration example of an endoscope diagnosis support system according to a first embodiment of the present invention.

FIG. 1 is a block diagram illustrating a configuration example of an endoscope diagnosis support system 1 according to a first embodiment of the present invention. In FIG. 1, illustration of a signal line that connects an operation unit X to a control unit 32 for setting an observation mode is omitted.

The endoscope diagnosis support system 1 includes a light source drive unit 11, an endoscope 21, a video processor 31, a display unit 41, and the operation unit X. The light source drive unit 11 is connected to the endoscope 21 and the video processor 31. The endoscope 21 and the operation unit X are connected to the video processor 31. The video processor 31 is connected to the display unit 41.

The light source drive unit 11 is a circuit configured to drive an illumination portion 23 disposed in a distal end portion of an insertion portion 22 of the endoscope 21. The light source drive unit 11 is connected to the control unit 32 in the video processor 31 and the illumination portion 23 in the endoscope 21. The light source drive unit 11 emits illumination light from the illumination portion 23 to a subject under control of the control unit 32. The light source drive unit 11 emits normal light and narrow band light from the illumination portion 23 in accordance with the observation mode. More specifically, when the observation mode is a normal light mode, the light source drive unit 11 emits the normal light from the illumination portion 23, and when the observation mode is a narrow band light observation mode, the light source drive unit 11 emits the narrow band light from the illumination portion 23.

The endoscope 21 is configured such that image pickup of an inside of the subject can be performed. The endoscope 21 includes the insertion portion 22, the illumination portion 23, and an image pickup portion 24.

The insertion portion 22 is formed to be elongated so as to be able to be inserted into the subject. The insertion portion 22 includes a conduit such as a treatment instrument insertion conduit that is not illustrated in the drawing. The insertion portion 22 can cause a treatment instrument that is not illustrated in the drawing which is allowed to be inserted into the treatment instrument insertion conduit to protrude from the distal end portion thereof.

The illumination portion 23 is disposed in the distal end portion of the insertion portion 22 and emits the illumination light to the subject under control of the light source drive unit 11.

The image pickup portion 24 is disposed in the distal end portion of the insertion portion 22, performs image pickup of the subject to which the illumination light is emitted, and outputs an image pickup signal to the video processor 31.

The video processor 31 performs control on the endoscope 21, generates an endoscope image A based on the image pickup signal inputted from the endoscope 21, and generates a display image B based on the endoscope image A. The video processor 31 includes the control unit 32, an anomaly detection unit 33, and an image generation unit 34.

The control unit 32 is a circuit configured to control the respective units in the endoscope diagnosis support system 1. The control unit 32 performs image processing such as gain adjustment, white balance adjustment, gamma correction, contour enhancement correction, or enlargement/reduction adjustment based on the image pickup signal inputted from the endoscope 21, for example, to generate the endoscope image A, and outputs the endoscope image A to the anomaly detection unit 33 and the image generation unit 34. The control unit 32 transmits a control signal to the light source drive unit 11 and drives the illumination portion 23 in accordance with the observation mode. The observation mode is set by an instruction input of a user via the operation unit X. The control unit 32 may also adjust a light emitting amount of the illumination portion 23 in accordance with a luminance of the endoscope image A. The endoscope image A may be either a moving or a still image.

The anomaly detection unit 33 is a circuit configured to perform detection of an anomaly candidate area L that is an area corresponding to a candidate of an anomaly such as a lesion based on the endoscope image A. The anomaly detection unit 33 is connected to the image generation unit 34. When the anomaly candidate area L is not detected, the image generation unit 34 outputs a detection result indicating non-detection of the anomaly candidate area L to the image generation unit 34. When the anomaly candidate area L is detected, the anomaly detection unit 33 outputs a detection result indicating a detection position and a size of the anomaly candidate area L to the image generation unit 34. In other words, the anomaly detection unit 33 performs the detection of the anomaly candidate area L from the endoscope image A obtained by performing image pickup of the inside of the subject by the image pickup portion 24 and outputs the detection result. The anomaly candidate area L is a lesion candidate area.

For example, the anomaly detection unit 33 is configured by a computing apparatus using an artificial intelligence technology such as machine learning.

More specifically, the anomaly detection unit 33 is configured by a computing apparatus that learns extraction of a feature value by a deep learning technology. The anomaly detection unit 33 performs predetermined computation adjusted by the learning with respect to the endoscope image A inputted from the image pickup portion 24, and outputs a feature value indicating non-detection of the anomaly candidate area L or a feature value indicating the detection position and the size of the anomaly candidate area L to the image generation unit 34 as the detection result.

Note that the anomaly detection unit 33 is configured by the computing apparatus using the artificial intelligence technology, but may also be configured by a computing apparatus that does not use the artificial intelligence technology. For example, the anomaly detection unit 33 may be configured to perform extraction of a contour from a change amount between mutually adjacent pixels, and perform the extraction of the feature value by matching between the contour and model information of the anomaly candidate area L which is previously stored in the control unit 32.

The image generation unit 34 is a circuit configured to generate the display image B. The image generation unit 34 performs generation of the display image B based on the endoscope image A inputted from the control unit 32, the detection result inputted from the anomaly detection unit 33, and an instruction signal inputted from the operation unit X. The image generation unit 34 switches a detection position image D1 in a main area B1 from a non-display state to the display state in accordance with the instruction signal.

The display unit 41 is configured such that the display image B inputted from the image generation unit 34 can be displayed on a display screen. The display unit 41 is, for example, a monitor including a rectangular display screen.

The operation unit X is configured such that instruction input can be performed by a user operation. The operation unit X is connected to the image generation unit 34. The operation unit X includes a foot switch Xa, a keyboard Xb, a tablet Xc, a voice input apparatus Xd, and a scope switch Xe. Hereinafter, the operation unit X is mentioned when the foot switch Xa, the keyboard Xb, the tablet Xc, the voice input apparatus Xd, and the scope switch Xe are wholly or partly illustrated.

The foot switch Xa, the keyboard Xb, the tablet Xc, and the voice input apparatus Xd are connected to the video processor 31 in a wired or wireless manner A stepping operation on a pedal by a foot of the user can be performed by the foot switch Xa. A pressing operation on a predetermined key by a hand or finger of the user can be performed by the keyboard Xb. A touch operation on a touch panel by the hand or finger of the user can be performed by the tablet Xc. An operation based on voice of the user can be performed by the voice input apparatus Xd. In the voice input apparatus Xd, the voice of the user is inputted, and predetermined voice for instructing the display state or the non-display state is detected from the inputted voice. The scope switch Xe is attached to the endoscope 21, and the operation by the hand or finger of the user can be performed.

When the instruction input for instructing the display state is performed by the hand or finger, the foot, or the voice of the user, the operation unit X outputs the instruction signal for instructing the display state to the image generation unit 34. When the instruction input for instructing the non-display state is performed by the hand or finger, the foot, or the voice of the user, the operation unit X outputs the instruction signal for instructing the non-display state to the image generation unit 34. In other words, the operation unit X outputs the instruction signal in accordance with the operation of the user.

(Configuration of Display Image B)

A configuration of the display image B is described.

Figure 2:
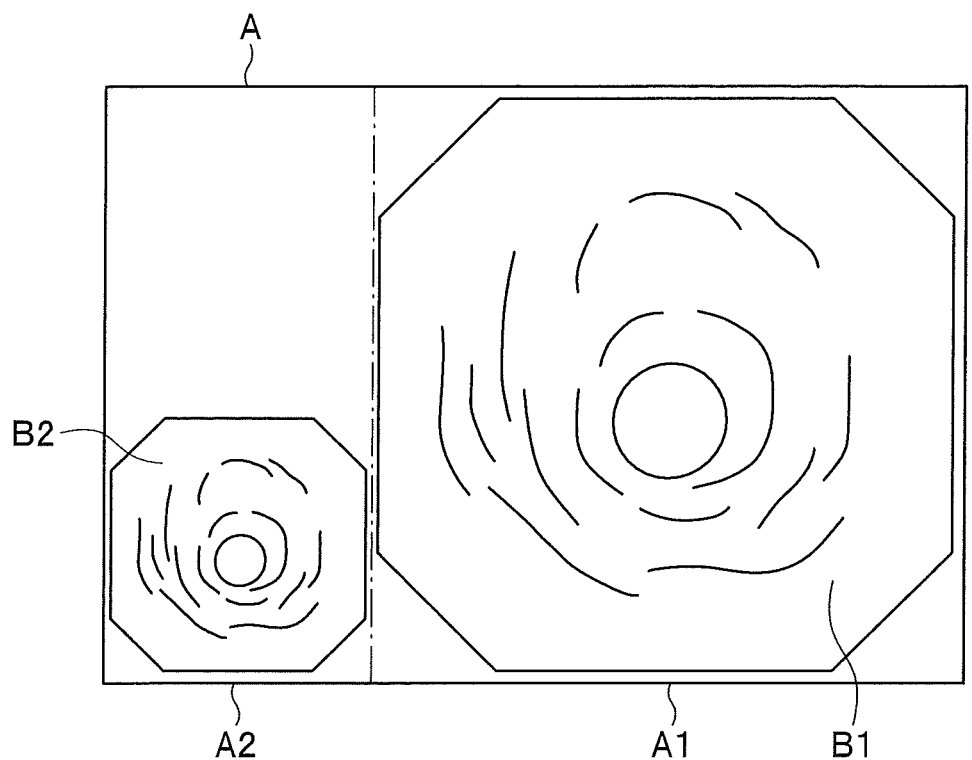
FIG. 2 is a diagram illustrating a configuration example of a display image of a display unit of the endoscope diagnosis support system according to the first embodiment of the present invention.

FIG. 2 is a diagram illustrating a configuration example of the display image B of the display unit 41 of the endoscope diagnosis support system 1 according to the first embodiment of the present invention. In the example of FIG. 2, entire shapes of endoscope images A1 and A2 are octagonal, and a lumen in a living body is schematically represented by curved lines.

The display image B is a rectangular image and includes the main area B1 and a sub area B2 that are divided in a longitudinal direction. A dashed-dotted line in FIG. 2 is a virtual line indicating a boundary between the main area B1 and the sub area B2.

The main area B1 is an area in which an endoscope image A1 is displayed. The main area B1 is set to be wider than the sub area B2 such that visibility of the endoscope image A1 can be improved. The endoscope image A1 is displayed to have a size larger than the endoscope image A2 in the main area B1.

Figure 4:
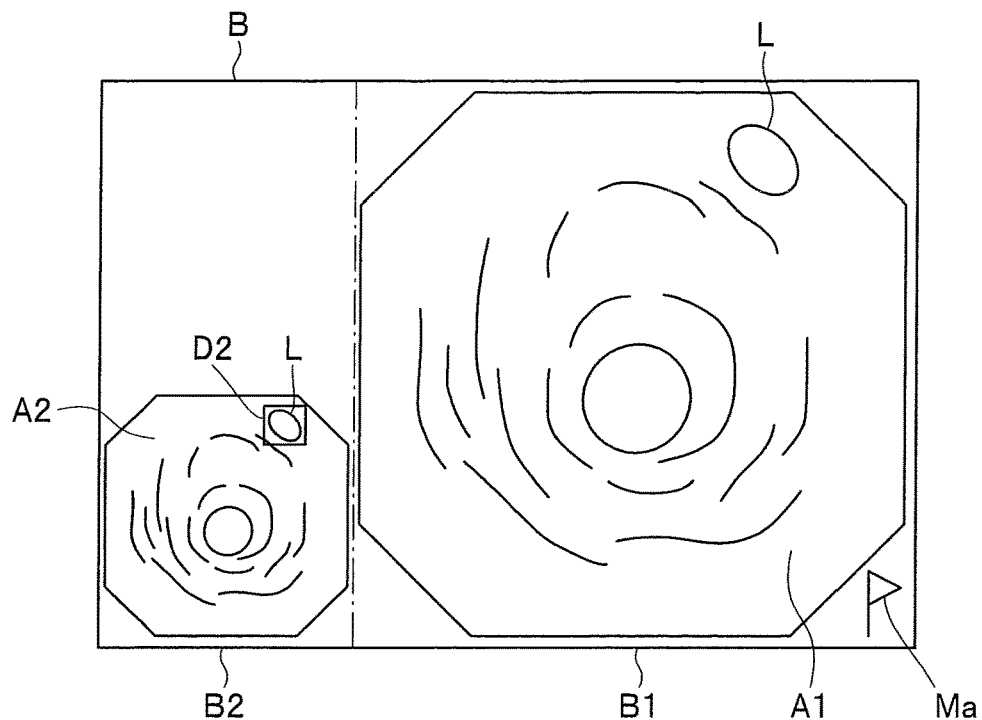
FIG. 4 is a diagram illustrating a configuration example of the display image of the display unit of the endoscope diagnosis support system according to the first embodiment of the present invention.

The sub area B2 is an area where the detection position of the anomaly candidate area L is displayed. The sub area B2 is arranged so as to be adjacent to the main area B1. The endoscope image A2 for superposing a detection position image D2 for indicating a detection position is arranged in the sub area B2 (FIG. 4).

(Operation)

Subsequently, display image generation processing of the image generation unit 34 is described.

Figure 3:
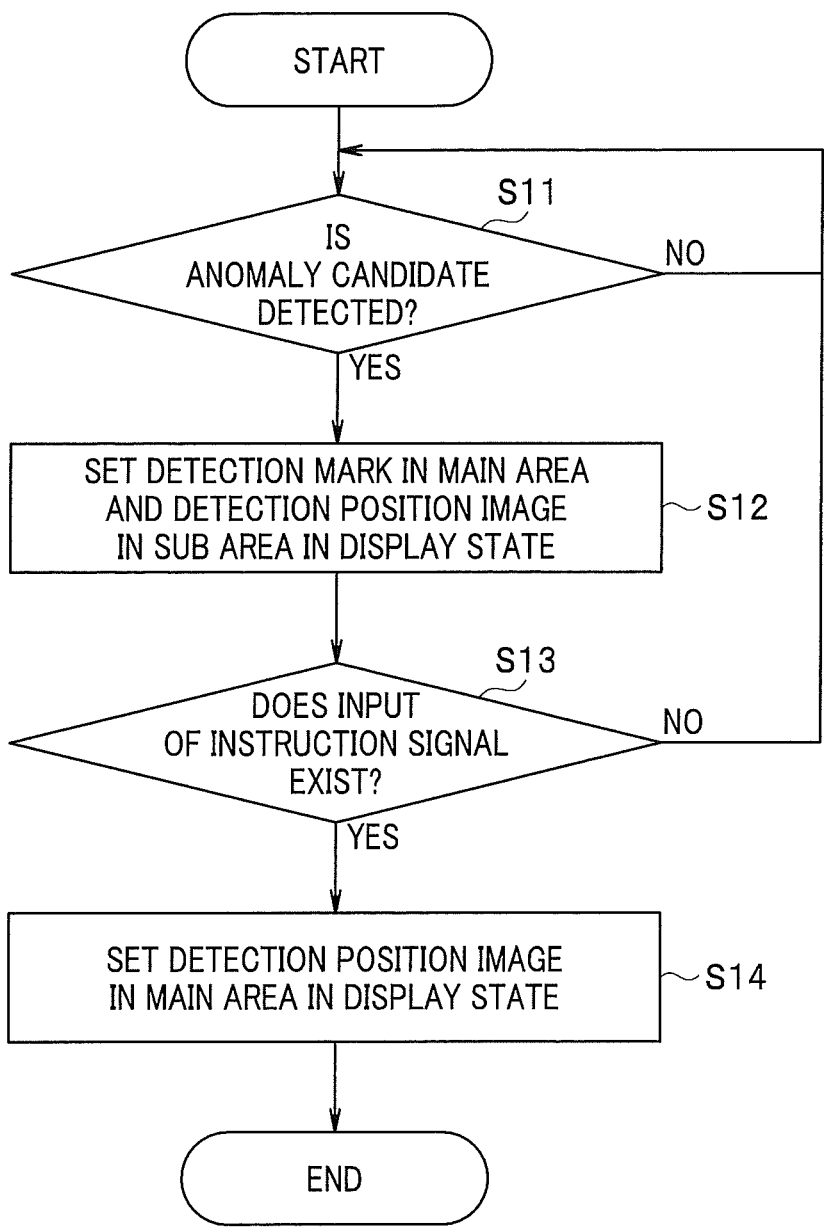
FIG. 3 is a flowchart illustrating an example of display image generation processing of the endoscope diagnosis support system according to the first embodiment of the present invention.
Figure 5:
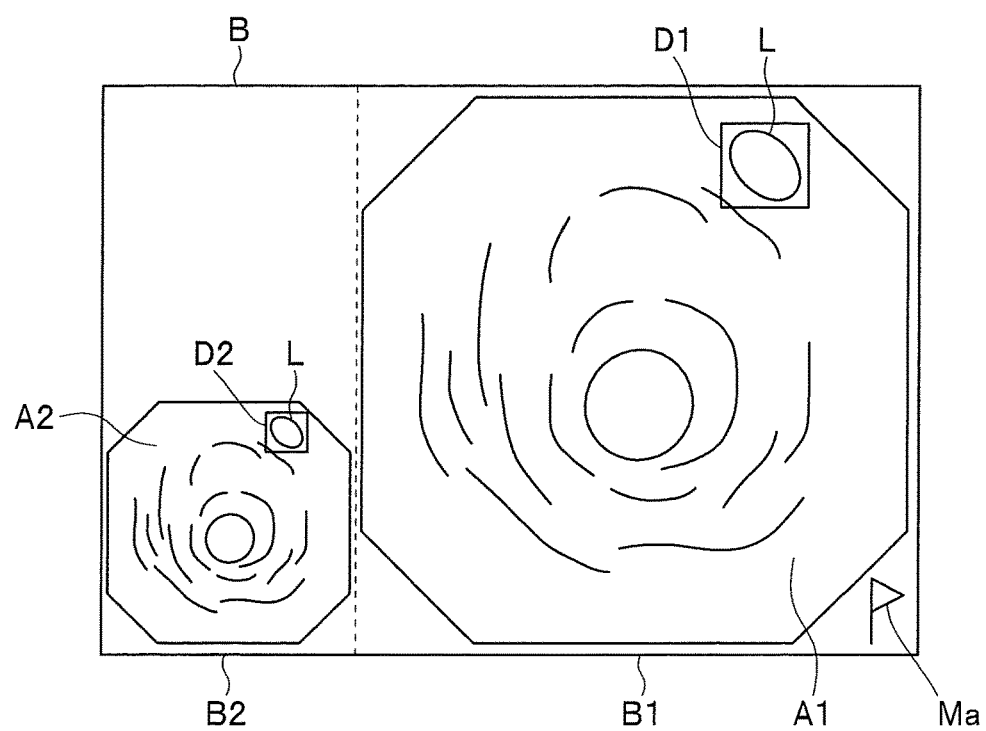
FIG. 5 is a diagram illustrating a configuration example of the display image of the display unit of the endoscope diagnosis support system according to the first embodiment of the present invention.

FIG. 3 is a flowchart illustrating an example of the display image generation processing of the endoscope diagnosis support system 1 according to the first embodiment of the present invention. FIG. 4 and FIG. 5 are diagrams illustrating a configuration example of the display image B of the display unit 41 of the endoscope diagnosis support system 1 according to the first embodiment of the present invention.

When the insertion portion 22 is inserted to perform image pickup of the subject, the image pickup portion 24 outputs the image pickup signal to the control unit 32. The control unit 32 performs the image processing such as the gain adjustment, the white balance adjustment, the gamma correction, the contour enhancement correction, or the enlargement/reduction adjustment based on the image pickup signal and outputs the endoscope image A to the anomaly detection unit 33 and the image generation unit 34.

The anomaly detection unit 33 performs predetermined computation and outputs the detection result to the image generation unit 34.

The image generation unit 34 adjusts the size of the endoscope image A inputted from the control unit 32, arranges the endoscope image A1 in the main area B1, and arranges the endoscope image A2 in the sub area B2.

It is determined whether or not the anomaly candidate area L is detected (S11). When the image generation unit 34 determines that the detection result indicating non-detection of the anomaly candidate area L is inputted from the anomaly detection unit 33 (S11: NO), the process repeats S11. On the other hand, as illustrated in FIG. 4, when the image generation unit 34 determines that the detection result indicating the detection position and the size of the anomaly candidate area L is inputted (S11: YES), the process proceeds to S12.

A detection mark Ma in the main area B1 and the detection position image D2 in the sub area B2 are set in the display state (S12). The image generation unit 34 sets the detection mark Ma corresponding to an anomaly detection image indicating detection of the anomaly candidate area L in the display state in a lower right portion in the main area B1 and also outside of the endoscope image A1. In other words, the detection mark Ma is arranged in a periphery portion of the main area B1 and also in a vicinity of the endoscope image A1. In the example of FIG. 4, the detection mark Ma is an image imitating a flag, but another image may also be adopted.

The image generation unit 34 also sets the detection position image D2 in the display state based on the detection result such that a position corresponding to the detection position of the anomaly candidate area L in the sub area B2 is indicated. In the example of FIG. 4, the detection position image D2 is a rectangular frame image, but another image may also be adopted.

It is determined whether or not an input of the instruction signal exists (S13). When the image generation unit 34 determines that the input of the instruction signal for instructing the display state does not exist, the process returns to S11. On the other hand, when the image generation unit 34 determines that the input of the instruction signal for instructing the display state exists, the process proceeds to S14.

The detection position image D1 in the main area B1 is set in the display state (S14). As illustrated in FIG. 5, the image generation unit 34 sets the detection position image D1 for indicating the detection position in the display state such that a position corresponding to the detection position of the anomaly candidate area L in the main area B1 is indicated. In the example of FIG. 5, the detection position image D1 is a rectangular frame image, but another image may also be adopted. In other words, the detection position image D1 arranged in the main area B1 is a rectangular frame image.

When the instruction input for instructing the non-display state by the operation unit X exists or the anomaly candidate area L is not detected, the image generation unit 34 sets the detection position image D1 in the non-display state.

The processes S11 to S14 constitute the display image generation processing according to the first embodiment.

In other words, the image generation unit 34 is divided into the main area B1 and the sub area B2 that is smaller than the main area B1, the endoscope image A1 is arranged in the main area B1, and the display image B in which the anomaly detection image indicating detection of the anomaly candidate area L is arranged in the periphery portion of the main area B1 is generated in accordance with the detection result. The image generation unit 34 arranges the detection position image D2 for indicating the detection position such that the position corresponding to the detection position of the anomaly candidate area L in the sub area B2 is indicated in accordance with the detection result. After the display image B in which the anomaly detection image is arranged in the main area B1 is generated, the image generation unit 34 arranges the detection position image D1 such that the position corresponding to the detection position in the main area B1 is indicated.

In other words, according to an endoscope diagnosis support method, the anomaly detection unit 33 performs the detection of the anomaly candidate area L from the endoscope image A obtained by performing image pickup of the inside of the subject by the image pickup portion 24 to output the detection result, and the image generation unit 34 generates the display image B which is divided into the main area B1 and the sub area B2 that is smaller than the main area B1 and in which the endoscope image A1 is arranged in the main area B1, and the anomaly detection image indicating detection of the anomaly candidate area L is arranged in the periphery portion of the main area B1 in accordance with the detection result.

According to this, in the endoscope diagnosis support system 1, the detection position image D1 in the anomaly candidate area L in the main area B1 is set in the non-display state until the user performs the instruction input, and user's attention to the endoscope image A1 is not disturbed.

According to the above-described first embodiment, in the endoscope diagnosis support system 1, the anomaly candidate area L corresponding to the candidate of the anomaly such as the lesion can be indicated in a manner that the user's attention to the endoscope image A1 is not disturbed, and the diagnosis based on the endoscope 21 can be supported.

First Modification of First Embodiment

According to the first embodiment, the detection mark Ma is displayed in the lower right portion in the main area B1, but a detection mark Mb may be displayed in four corners of the endoscope image A1.

Figure 6:
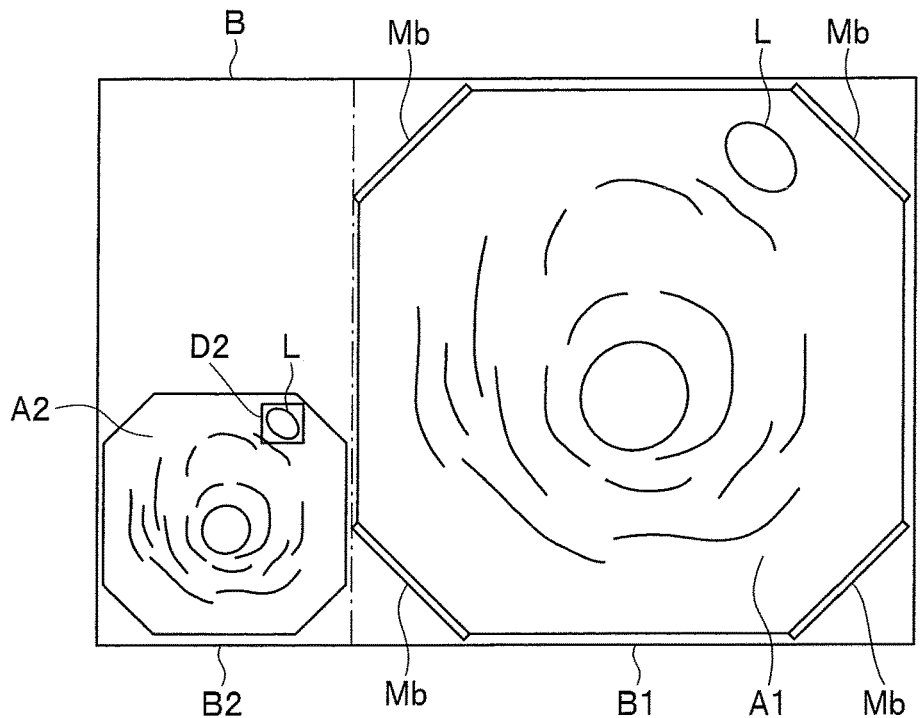
FIG. 6 is a diagram illustrating a configuration example of the display image of the display unit of the endoscope diagnosis support system according to a first modification of the first embodiment of the present invention.
Figure 7:
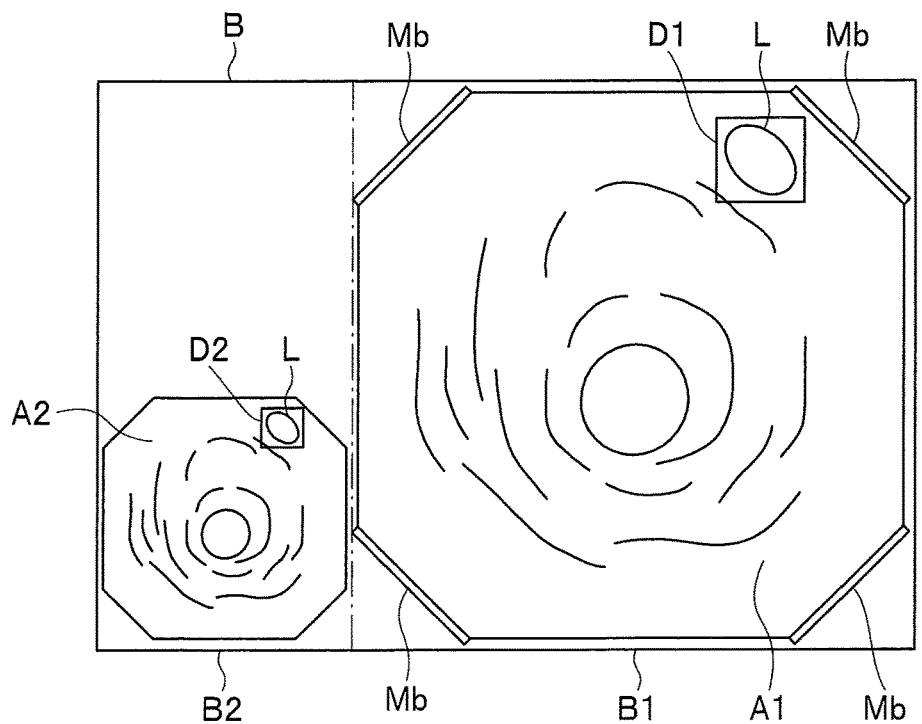
FIG. 7 is a diagram illustrating a configuration example of the display image of the display unit of the endoscope diagnosis support system according to the first modification of the first embodiment of the present invention.

FIG. 6 and FIG. 7 are diagrams illustrating a configuration example of the display image B of the display unit 41 of the endoscope diagnosis support system 1 according to a first modification of the first embodiment of the present invention. According to the present modification, descriptions of same components as those according to other embodiments and modifications are omitted.

As illustrated in FIG. 6, when the detection result indicating the detection position and the size of the anomaly candidate area L is inputted from the anomaly detection unit 33, the image generation unit 34 sets the detection mark Mb in the main area B1 in the display state, and sets the detection position image D2 in the sub area B2 in the display state.

In the example of FIG. 6, the detection marks Mb are arranged in the periphery portions of the main area B1 and also outside of the endoscope image A1 along tapered portions of the four corners of the endoscope image A1. The detection mark Mb is a strip-like image having a predetermined thickness. Note that in the example of FIG. 6, the detection mark Mb is arranged in all of the four corners of the endoscope image A1, but may be configured to be arranged in at least part of the four corners instead of all of the four corners.

As illustrated in FIG. 7, when the user performs the instruction input of the display state by the operation unit X, the detection position image D1 in the main area B1 is set in the display state.

In other words, the image generation unit 34 arranges the detection mark Mb in the four corners of the endoscope image A1.

According to this, in the endoscope diagnosis support system 1, the detection mark Mb can be displayed such that the user can more easily notice.

Second Modification of First Embodiment

According to the first modification of the first embodiment, the detection mark Mb of the strip-like image is displayed, but a detection mark Mc of a triangular image may be displayed.

Figure 8:
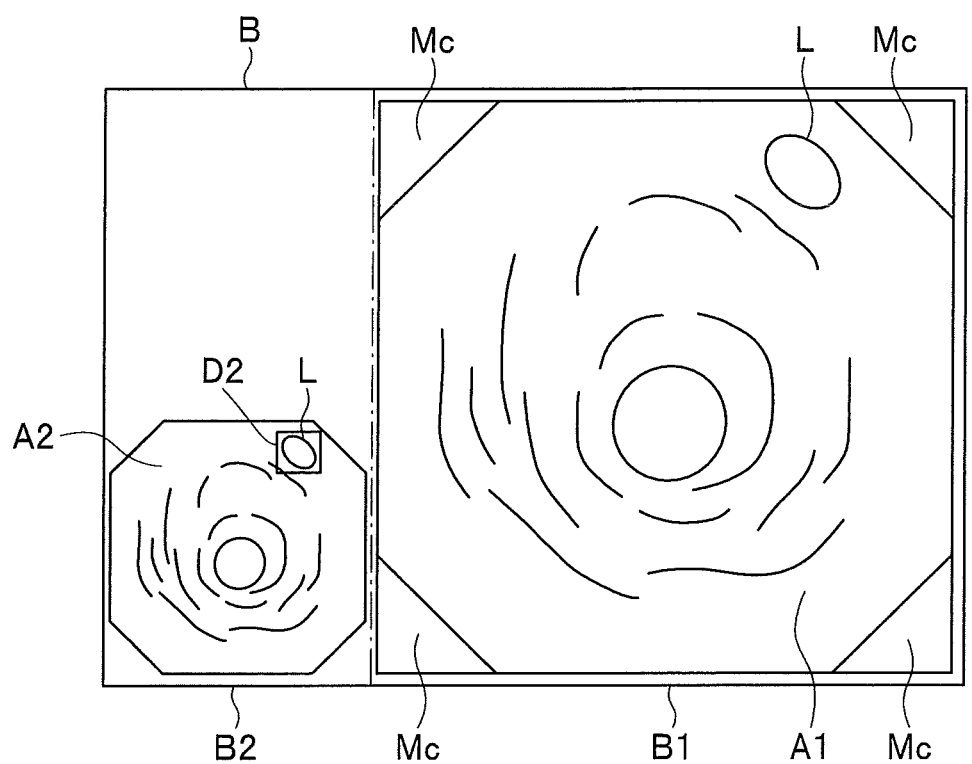
FIG. 8 is a diagram illustrating a configuration example of the display image of the display unit of the endoscope diagnosis support system according to a second modification of the first embodiment of the present invention.

FIG. 8 is a diagram illustrating a configuration example of the display image B of the display unit 41 of the endoscope diagnosis support system 1 according to a second modification of the first embodiment of the present invention. According to the present modification, descriptions of same components as those according to other embodiments and modifications are omitted.

In the example of FIG. 8, the detection mark Mc is arranged in the periphery portions in the main area B1 and also outside of the endoscope image A1 along the tapered portions of the four corners of the endoscope image A1. The detection mark Mc is a triangular image marked out by a predetermined color. Note that in the example of FIG. 8, the detection mark Mc is arranged in all of the four corners of the endoscope image A1, but may be configured to be arranged in at least part of the four corners instead of all of the four corners.

According to this, in the endoscope diagnosis support system 1, the detection mark Mc can be displayed such that the user can more easily notice.

Third Modification of First Embodiment

According to the first embodiment and first and second modifications of the first embodiment, entire shapes of the endoscope images A1 and A2 are octagonal, but may be other than an octagon.

Figure 9:
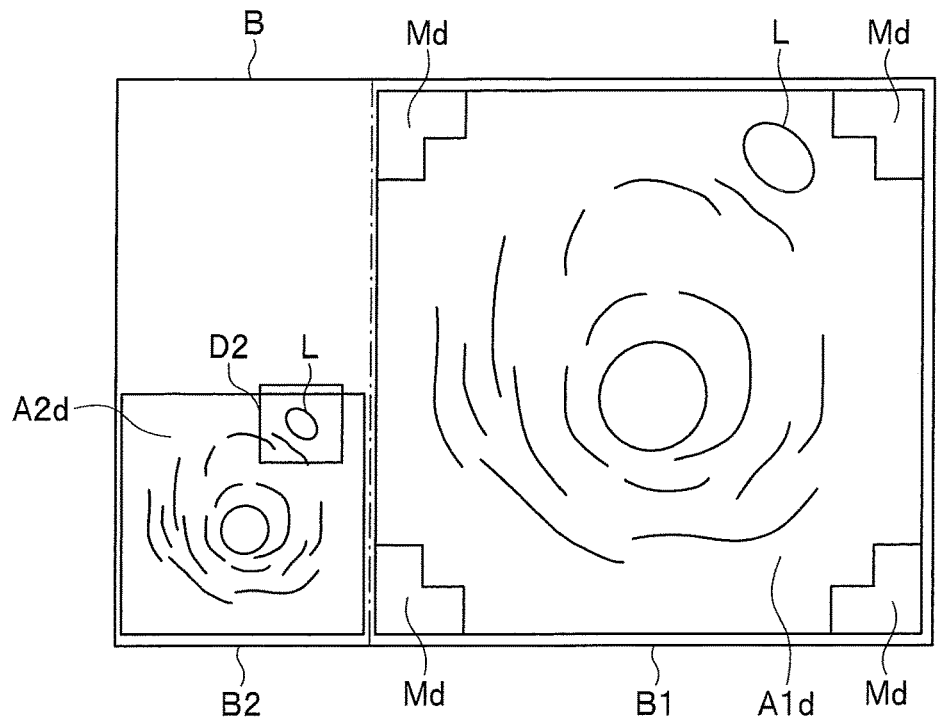
FIG. 9 is a diagram illustrating a configuration example of the display image of the display unit of the endoscope diagnosis support system according to a third modification of the first embodiment of the present invention.

FIG. 9 is a diagram illustrating a configuration example of the display image B of the display unit 41 of the endoscope diagnosis support system 1 according to a third modification of the first embodiment of the present invention. According to the present modification, descriptions of same components as those according to other embodiments and modifications are omitted.

An endoscope image A1d, an entire shape of which is quadrangular, is arranged in the main area B1, and an endoscope image A2d obtained by reducing the endoscope image A1d is arranged in the sub area B2.

In the example of FIG. 9, a detection mark Md is an L-shaped image that is arranged in the four corners of the endoscope image A1d and obtained by being bent along the four corners. Note that the detection mark Md may be displayed in a flashing manner so as to be conspicuous.

According to this, in the endoscope diagnosis support system 1, the detection mark Md can be displayed in the four corners of the endoscope image A1d, the entire shape of which is quadrangular, such that the user can more easily notice.

Fourth Modification of First Embodiment

According to the third modification of the first embodiment, the entire shapes of the endoscope images A1d and A2d are quadrangular, but mutually facing sides may be curved.

Figure 10:
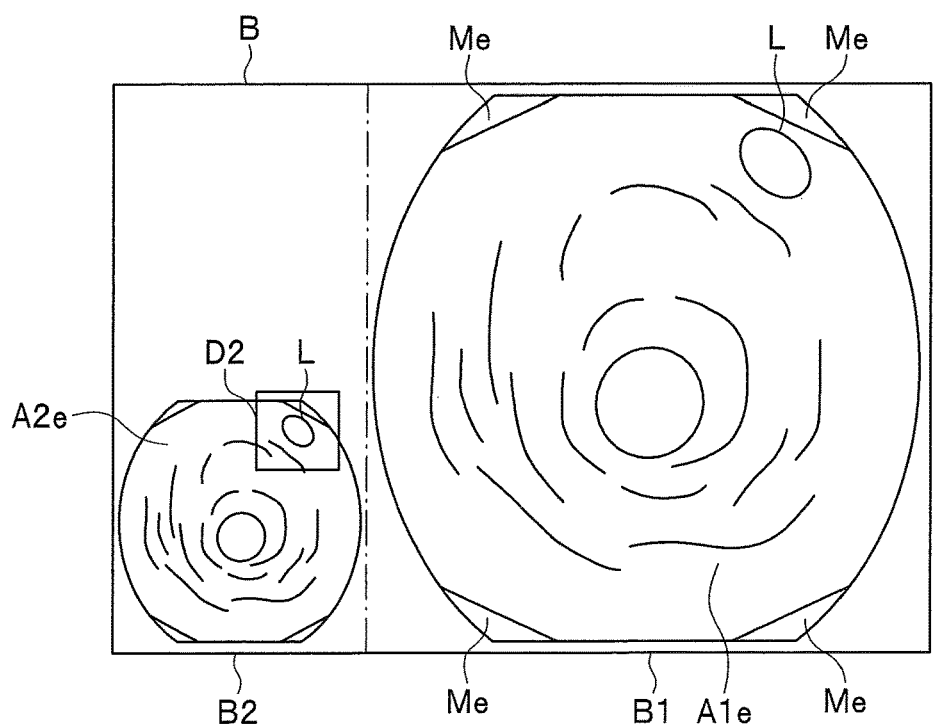
FIG. 10 is a diagram illustrating a configuration example of the display image of the display unit of the endoscope diagnosis support system according to a fourth modification of the first embodiment of the present invention.

FIG. 10 is a diagram illustrating a configuration example of the display image B of the display unit 41 of the endoscope diagnosis support system 1 according to a fourth modification of the first embodiment of the present invention. According to the present modification, descriptions of same components as those according to other embodiments and modifications are omitted.

An endoscope image A1e in which upper and lower portions are linear and also both side portion on left and right are curved is arranged in the main area B1, and an endoscope image A2e obtained by reducing the endoscope image A1e is arranged in the sub area B2.

In the example of FIG. 10, a detection mark Me is a triangular image that is arranged in the four corners in the endoscope image A1e and obtained by shaping one side curved.

According to this, in the endoscope diagnosis support system 1, the detection mark Me can be displayed in the four corners of the endoscope image A1e in which the mutually facing sides are curved such that the user can more easily notice.

Fifth Modification of First Embodiment

According to the first embodiment and the first to fourth modifications of the first embodiment, the instruction input for setting the detection position image D1 in the display state is performed by an operation on the operation unit X, but a movement of a user's eyes may be detected to set the detection position image D1 in the display state.

Figure 11:
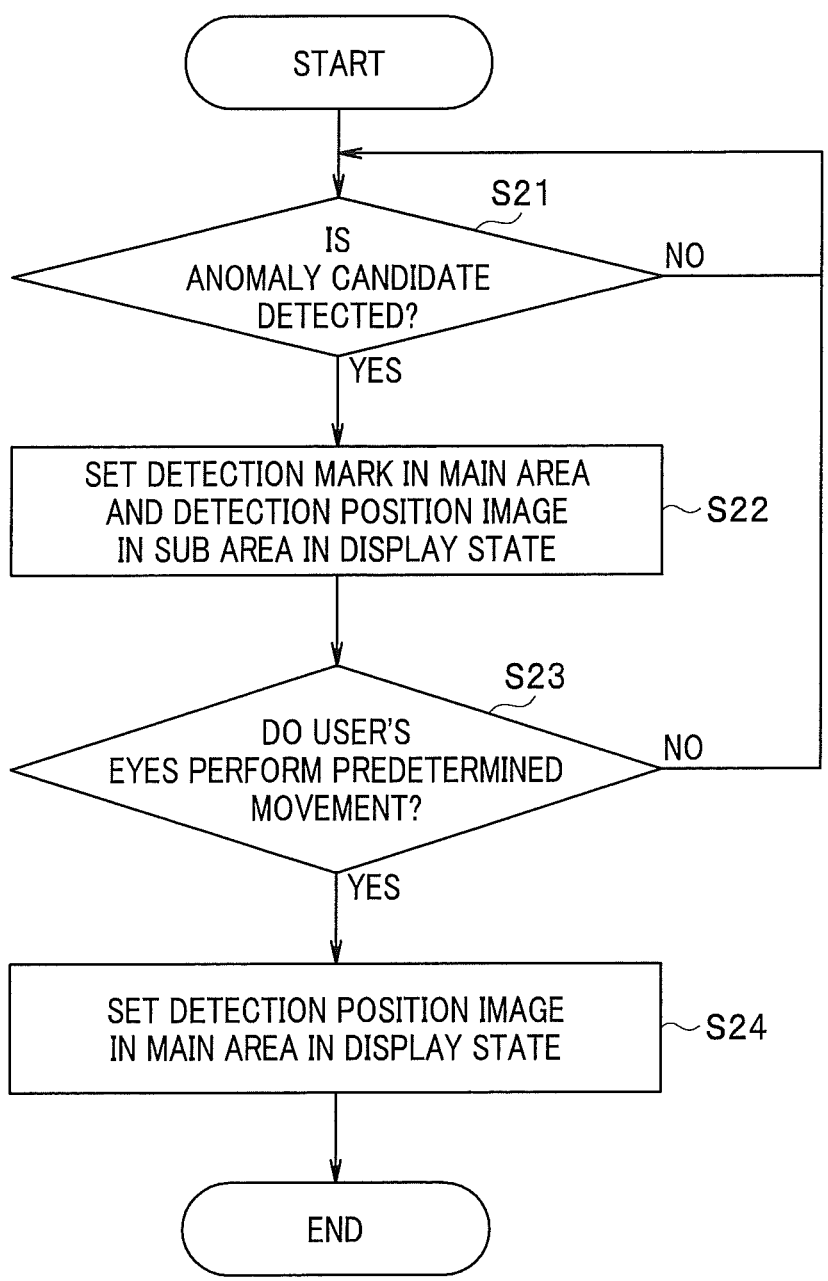
FIG. 11 is a flowchart illustrating an example of the display image generation processing of the endoscope diagnosis support system according to a fifth modification of the first embodiment of the present invention.
Figure 12:
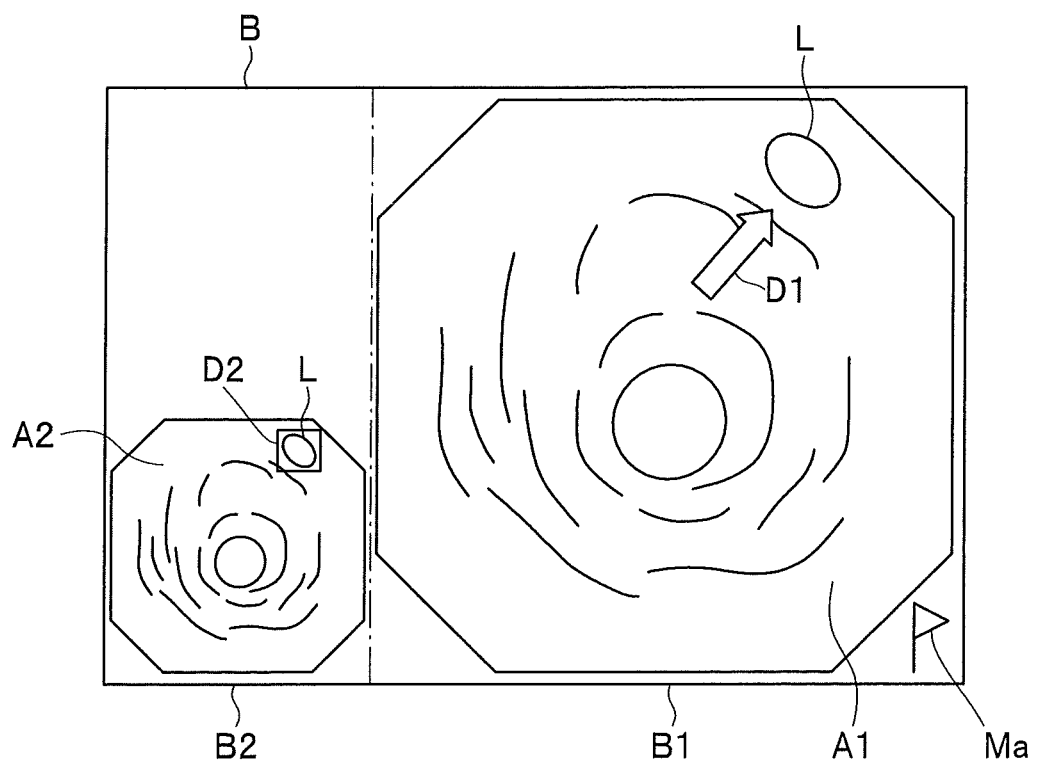
FIG. 12 is a diagram illustrating a configuration example of the display image of the display unit of the endoscope diagnosis support system according to the fifth modification of the first embodiment of the present invention.

FIG. 11 is a flowchart illustrating an example of the display image generation processing of the endoscope diagnosis support system 1 according to a fifth modification of the first embodiment of the present invention. FIG. 12 is a diagram illustrating a configuration example of the display image B of the display unit 41 of the endoscope diagnosis support system 1 according to the fifth modification of the first embodiment of the present invention.

According to the present embodiment, descriptions of same components as those according to other embodiments and modifications are omitted.

According to the present modification, the endoscope diagnosis support system 1 includes a camera Z (dashed-two dotted line in FIG. 1).

The camera Z is attached to a rim or the like of the display unit 41 such that the movement of the user's eyes which observe the endoscope image A1 can be detected, for example. The camera Z is connected to the image generation unit 34. The camera Z performs image pickup of the user's eyes and outputs an image of the user's eyes to the image generation unit 34.

Subsequently, an operation of the present modification is described.

Since S21 and S22 are same as S11 and S12, descriptions thereof are omitted.

It is determined whether or not the user's eyes perform a predetermined movement (S23). When the image generation unit 34 determines that the user's eyes do not perform the predetermined movement, the process returns to 21. On the other hand, when the image generation unit 34 determines that the user's eyes perform the predetermined movement, the process proceeds to S24.

The predetermined movement may be a movement where, for example, the user finds an anomaly in the endoscope image A by visual observation, and a line of sight of the user directs to the detection position of the anomaly candidate area L for a predetermined period of time. The predetermined movement may also be a movement where the user notices the detection mark Ma, and the line of sight of the user shifts from the main area B1 to the entirety of the display image B. The predetermined movement may also be a movement where the line of sight of the user directs to a previously set predetermined position in the display image B.

The detection position image D1 in the main area B1 is set in the display state (S24). The detection position image D1 is an arrow image displayed in a vicinity of the anomaly candidate area L in the main area B1. The detection position image D1 arranged in the main area B1 is an arrow image.

The image generation unit 34 sets the detection position image D1 in the non-display state based on the instruction input by the operation unit X, the detection of the predetermined movement of the eyes by the camera Z, or the non-detection of the anomaly candidate area L.

The image generation unit 34 sets non-display of the detection position image D1 in the main area B1 such that the user's attention to the endoscope image A1 is not disturbed when the observation mode is switched from a normal observation mode to a narrow band light mode.

A treatment instrument detection portion T1 (dashed-two dotted line in FIG. 1) configured to detect a predetermined treatment instrument from the endoscope image A is included in the anomaly detection unit 33, and when the predetermined treatment instrument is detected from the endoscope image A, the detection position image D1 in the main area B1 is set in the non-display such that the user's attention is not disturbed.

In other words, when the image generation unit 34 determines that a predetermined display switching condition is satisfied, the image generation unit 34 switches the detection position image D1 in the main area B1 to either the display state or the non-display state. The predetermined display switching condition is whether or not the image of the user's eyes which is inputted from the camera Z indicates the predetermined movement. The predetermined display switching condition is also whether or not the observation mode is the narrow band light observation mode. The predetermined display switching condition is also whether or not the predetermined treatment instrument is detected by the treatment instrument detection portion T1.

The processes S21 to S24 constitute the display image generation processing according to a fifth modification of the first embodiment.

According to this, in the endoscope diagnosis support system 1, the detection position image D1 can be switched to either the display state or the non-display state by the predetermined display switching condition, which saves trouble of the user from operating the operation unit X.

Second Embodiment

According to the first embodiment and the first to fifth modifications of the first embodiment, the sub area B2 displays the detection position of the anomaly candidate area L, but may display an enlarged image E of the anomaly candidate area L.

Figure 13:
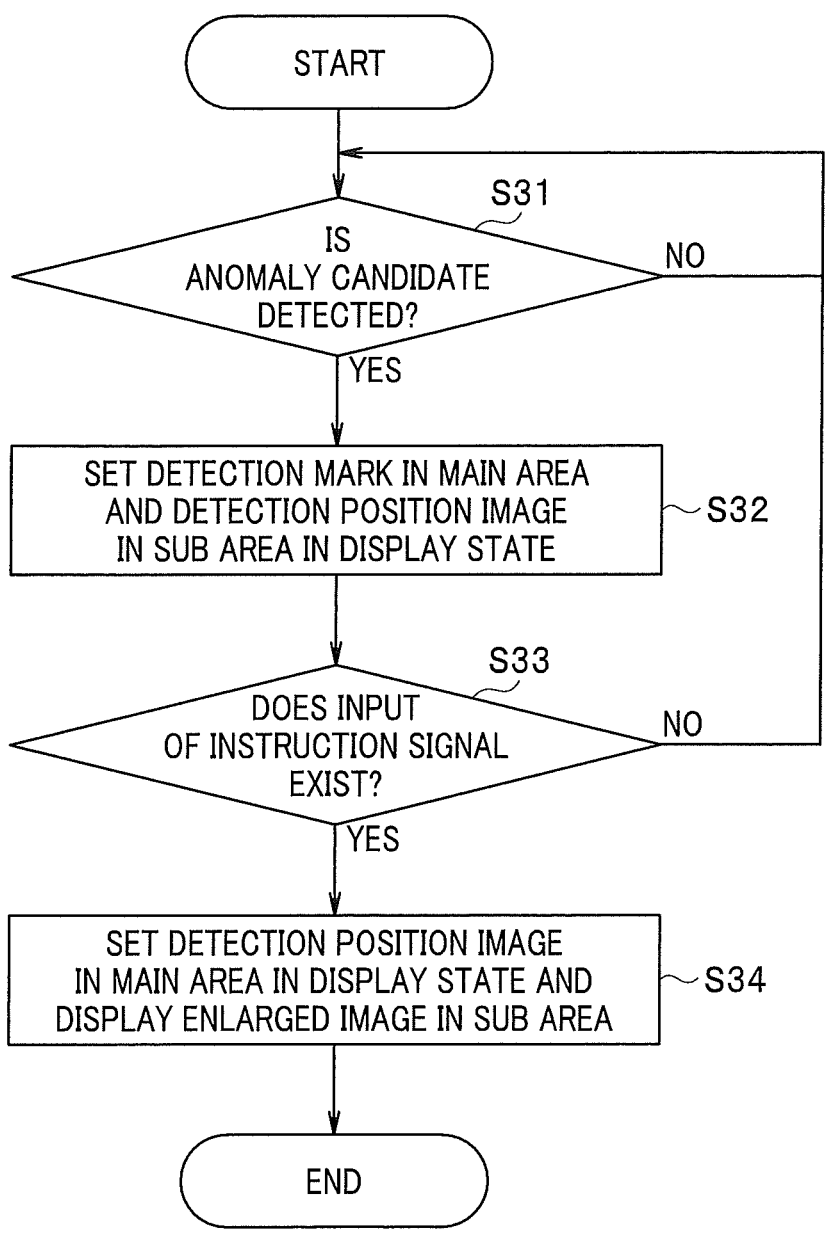
FIG. 13 is a flowchart illustrating an example of the display image generation processing of the endoscope diagnosis support system according to a second embodiment of the present invention.
Figure 14:
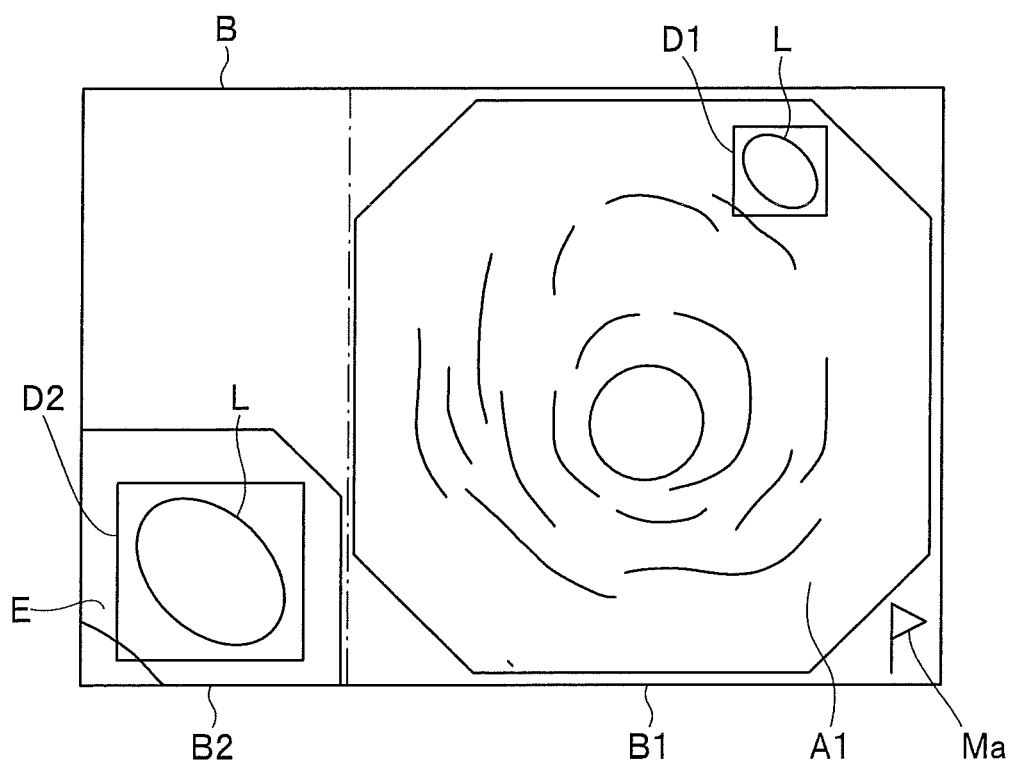
FIG. 14 illustrates a configuration example of the display image of the display unit of the endoscope diagnosis support system according to the second embodiment of the present invention.

FIG. 13 is a flowchart illustrating an example of the display image generation processing of the endoscope diagnosis support system 1 according to a second embodiment of the present invention. FIG. 14 is a diagram illustrating a configuration example of the display image B of the display unit 41 of the endoscope diagnosis support system 1 according to the second embodiment of the present invention. According to the present embodiment, descriptions of same components as those according to other embodiments and modifications are omitted.

An operation of the endoscope diagnosis support system 1 according to the second embodiment is described.

Since S31 to S33 are same as S11 to S13, descriptions thereof are omitted.

The detection position image D1 in the main area B1 is set in the display state, and the enlarged image E is displayed in the sub area B2 (S34). As illustrated in FIG. 14, the image generation unit 34 sets the detection position image D1 in the main area B1 in the display state. The image generation unit 34 also displays the enlarged image E at a predetermined enlargement rate in the sub area B2.

In other words, the image generation unit 34 arranges the enlarged image E obtained by enlarging the anomaly candidate area L in the sub area B2.

The processes S31 to S34 constitute the display image generation processing according to the second embodiment.

According to this, in the endoscope diagnosis support system 1, the enlarged image E can be displayed in the sub area B2 by the instruction input of the user, and visibility of the anomaly candidate area L is improved.

According to the second embodiment described above, in the endoscope diagnosis support system 1, the anomaly candidate area L corresponding to the candidate of the anomaly such as the lesion can be indicated in a manner that the user's attention to the endoscope image A1 is not disturbed, and the diagnosis based on the endoscope 21 can be supported.

Note that according to the embodiments and the modifications, the detection marks Ma, Mb, Mc, Md, and Me and the detection position images D1 and D2 may have a same color such that it is easy for the user to see.

Note that according to the embodiments and the modifications, the image generation unit 34 may generate the display image B such that the detection position images D1 and D2 are not displayed outside of the endoscope images A1, A1d, A1e, A2, A2d, and A2e.

Note that according to the embodiments and the modifications, when the detection position image D1 is arranged in the main area B1, the image generation unit 34 also arranges the detection position image D2 in the sub area B2, but when the detection position image D1 is arranged in the main area B1, the display image B may be generated such that the detection position image D2 is not arranged in the sub area B2.

Note that according to the embodiments and the modifications, the operation unit X is configured by all of the foot switch Xa, the keyboard Xb, the tablet Xc, the voice input apparatus Xd, and the scope switch Xe, but may be configured by part of the foot switch Xa, the keyboard Xb, the tablet Xc, the voice input apparatus Xd, and the scope switch Xe. In other words, the operation unit X includes at least any one of the foot switch Xa, the keyboard Xb, the tablet Xc, the voice input apparatus Xd, and the scope switch Xe.

Note that according to the first embodiment, the detection mark Ma is displayed in the lower right portion in the main area B1, but may be displayed in an upper right portion, an upper left portion, or a lower left portion in the main area B1.

Note that according to the fifth modification of the first embodiment, the predetermined display switching condition is whether or not the image of the user's eyes indicates the predetermined movement, but a timer T2 may be included (dashed-two dotted line in FIG. 1), the anomaly detection unit 33 can detect an anomaly type in the anomaly candidate area L, the timer T2 can measure a predetermined period of time in accordance with the anomaly type after the anomaly candidate area L is detected, and the predetermined display switching condition may be whether or not the predetermined period of time elapses after the anomaly candidate area L is detected.

Note that the predetermined enlargement rate according to the second embodiment is previously set, but may be configured to change in accordance with the size of the anomaly candidate area L.

The respective "units" in the present specification are conceptual components corresponding to the respective functions of the embodiments and do not necessarily correspond to particular hardware or software routines on a one-on-one basis. Therefore, in the present specification, the embodiments are described while virtual circuit blocks (units) including the respective functions of the embodiments are supposed. With regard to the respective steps in the respective procedure according to the present embodiment, unless contrary to the nature thereof, an execution order may be changed, a plurality of steps may be executed at the same time, or the execution be performed in a different order for each execution. Furthermore, all or part of the respective steps in the respective procedure according to the present embodiment may be realized by hardware.

For example, the video processor 31 may include a central processing unit (CPU) 51 and a memory 52 and execute an endoscope diagnosis support program 53 stored in the memory 52 to realize the functions of the anomaly detection unit 33 and the image generation unit 34 (dashed-two dotted line in FIG. 1). In other words, the endoscope diagnosis support program 53 causes a computer to execute code for performing the detection of the anomaly candidate area L from the endoscope image A obtained by performing image pickup of the inside of the subject by the image pickup portion 24 to output the detection result, and code for generating the display image B which is divided into the main area B1 and the sub area B2 that is smaller than the main area B1 and in which the endoscope image A1 is arranged in the main area B1, and the anomaly detection image indicating the detection of the anomaly candidate area L is arranged in the periphery portion of the main area B1 in accordance with the detection result.

The present invention is not limited to the above-mentioned embodiments, and various modifications, alterations, and the like can be made in a range without departing from a gist of the present invention.

What is claimed is:

1. An endoscope diagnosis support system comprising:
a processor configured to:
generate an endoscope image based on an image pickup signal output by an endoscope, the image pick up signal being obtained by the endoscope performing image pickup of an inside of a subject;
perform detection of a candidate area from the endoscope image;
in response to detecting the candidate area,
acquire a position of the candidate area in the endoscope image; and
generate a first display image comprising:
a main area;

a sub area adjacent to the main area;
the endoscope image arranged in the main area;
a second endoscope image, based on the endoscope image in the main area, is further arranged in the sub area;
a plurality of detection indicators, indicating the detection of the candidate area, arranged in the main area so as to be located at a periphery of the endoscope image to surround the endoscope image; and
a detection position image separately arranged in the sub area, wherein a position of the detection position image in the sub area is set to correspond to the detected position of the candidate area in the endoscope image; and
in response to not detecting the candidate area, generate a second display image comprising the endoscope image arranged in the main area,
wherein the second display image does not include the detection position image and the plurality of detection indicators,
wherein the periphery of the endoscope image comprises:
a first periphery;
a second periphery adjacent to the first periphery; and
a third periphery adjacent to the second periphery, the second periphery being disposed between the first periphery and the third periphery, and
wherein in the first display image, the plurality of detection indicators comprises a first indicator at the first periphery and a second indicator at the third periphery, and no indicator of the plurality of detection indicators or another indicator is arranged in the second periphery.

2. The endoscope diagnosis support system according to claim 1,
wherein after the first display image in which the plurality of detection indicators are arranged in the main area is generated, the processor is configured to arrange a second detection position image in the main area, and
wherein the second detection position image indicates a position corresponding to the detection position of the candidate area.

3. The endoscope diagnosis support system according to claim 2,
wherein the processor is configured to generate the first display image in a manner that the second detection position image is not arranged outside of the endoscope image arranged in the main area.

4. The endoscope diagnosis support system according to claim 2,
wherein the second detection position image arranged in the main area is a rectangular frame image.

5. The endoscope diagnosis support system according to claim 2,
wherein the processor is configured to switch the second detection position image arranged in the main area to either a display state or a non-display state in accordance with an instruction signal indicating an instruction performed by a user.

6. The endoscope diagnosis support system according to claim 2, further comprising:
a camera,
wherein the processor is configured to:
determine whether a predetermined display switching condition is satisfied; and
switch the second detection position image in the main area to either a display state or a non-display state in accordance with a result of determining whether the predetermined display switching condition is satisfied,
wherein the predetermined display switching condition is an image of a user's eyes which is inputted from the camera indicates a predetermined movement.

7. The endoscope diagnosis support system according to claim 2, further comprising:
a timer,
wherein the processor is configured to:
determine whether a predetermined display switching condition is satisfied; and
switch the second detection position image in the main area to either a display state or a non-display state in accordance with a result of determining whether the predetermined display switching condition is satisfied, and
wherein the processor is configured to detect a type in the candidate area,
wherein the timer is configured to measure a predetermined period of time according to the type after the candidate area is detected, and
wherein the predetermined display switching condition is the predetermined period of time elapses after the candidate area is detected.

8. The endoscope diagnosis support system according to claim 2,
wherein the processor is configured to:
determine whether a predetermined display switching condition is satisfied; and
switch the second detection position image in the main area to either a display state or a non-display state in accordance with a result of determining whether the predetermined display switching condition is satisfied,
wherein the predetermined display switching condition is an observation mode is a narrow band light observation mode.

9. The endoscope diagnosis support system according to claim 2,
wherein the processor is configured to:
determine whether a predetermined display switching condition is satisfied; and
switch the second detection position image in the main area to either a display state or a non-display state in accordance with a result of determining whether the predetermined display switching condition is satisfied,
wherein the processor is configured to perform detection of a predetermined treatment instrument from the endoscope image, and
wherein the predetermined display switching condition is the processor detects the predetermined treatment instrument.

10. The endoscope diagnosis support system according to claim 2,
wherein when the second detection position image is arranged in the main area, the processor is configured to generate the first display image in a manner that the detection position image is not arranged in the sub area.

11. The endoscope diagnosis support system according to claim 1,
wherein the processor is configured to arrange an enlarged image, as the second image, obtained by enlarging the candidate area in the sub area.

12. The endoscope diagnosis support system according to claim 1, wherein the processor is configured to generate the first display image further comprising an image of a detection mark indicating detection of the candidate area in response to detecting the candidate area.

13. The endoscope diagnosis support system according to claim 1,
wherein the processor is configured to arrange the plurality of detection indicators in four corners of the endoscope image arranged in the main area to surround the endoscope image, in response to detecting the candidate area.

14. The endoscope diagnosis support system according to claim 1,
wherein when the plurality of detection indicators are arranged in the main area and the detection position image for indicating the detection position is arranged in the sub area, the processor is configured to generate the first display image in which the detection position image is not arranged in the main area.

15. The endoscope diagnosis support system according to claim 1,
wherein the processor is configured to arrange a detection position image in the first display image, and
wherein the detection position image indicates a detection position of the candidate area detected from the endoscope image.

16. The endoscope diagnosis support system according to claim 1,
wherein the plurality of detection indicators are arranged along parts of an outer edge of the endoscope image and each of the plurality of detection indicators are arranged separately.

17. The endoscope diagnosis support system according to claim 1,
wherein the plurality of detection indicators comprises a first line and a second line apart from the first line.

18. The endoscope diagnosis support system according to claim 1,
wherein the plurality of detection indicators comprises a first line and a second line facing the first line across the endoscope image.

19. The endoscope diagnosis support system according to claim 1,
wherein the first indicator at the first periphery of the endoscope image faces the second indicator at the third periphery of the endoscope image.

20. The endoscope diagnosis support system according to claim 1,
wherein the periphery of the endoscope image comprises a plurality of peripheries arranged in series, and
wherein the plurality of detection indicators are disposed on alternating ones of the plurality of peripheries to surround the endoscope image.

21. The endoscope diagnosis support system according to claim 1,
wherein the first periphery comprises a left curved periphery of the endoscope image and the third periphery comprises a right periphery of the endoscope image.

22. The endoscope diagnosis support system according to claim 1,
wherein the second periphery of the endoscope image is provided at a section of a periphery of the main area of the first display image, and
wherein the first periphery and the third periphery of the endoscope image are not arranged at the section of the periphery of the main area of the first display image.

23. The endoscope diagnosis support system according to claim 1, further comprising a display,
wherein both the main area and the sub area are displayed in the display.

24. The endoscope diagnosis support system according to claim 1,
wherein the candidate area is an anomaly candidate area, and the plurality of detection indicators is a plurality of anomaly detection indicators indicating the detection of the anomaly candidate area.

25. The endoscope diagnosis support system according to claim 1,
wherein all the plurality of detection indicators are activated in response to detecting the candidate area.

26. The endoscope diagnosis support system according to claim 1,
wherein the candidate area is an anomaly candidate area, and the plurality of detection indicators is a plurality of anomaly detection indicators indicating the detection of the anomaly candidate area, and
wherein the sub area is smaller than the main area, wherein all the plurality of detection indicators are activated in response to detecting the candidate area.

27. The endoscope diagnosis support system according to claim 1,
wherein the endoscope image arranged in the main area is the same image as the second image arranged in the sub area.

28. The endoscope diagnosis support system according to claim 1,
wherein the endoscope image has an upper periphery and a lower periphery, and
wherein in a horizontal direction of the endoscope image, the plurality of detection indicators is arranged between the upper periphery and the lower periphery.

29. The endoscope diagnosis support system according to claim 1,
wherein the processor is configured to:
in response to detecting the candidate area from the endoscope image, not arrange
a first detection position image in the main area of the first display image, and arrange a second detection position image, as the detection position image, in the sub area of the first display image; and
in response to not detecting the candidate area, not arrange the first detection position image in the main area of the first display image, and the second detection position image in the sub area of the first display image,
wherein the first detection position image indicates a detection position of the candidate area detected from the endoscope image.

30. The endoscope diagnosis support system according to claim 1,
wherein the endoscope image is an image generated by processing an image pickup signal.

31. A non-transitory storage medium that stores a computer-readable program for causing a computer to execute:
generating an endoscope image based on an image pickup signal output by an endoscope, the image pick up signal being obtained by the endoscope performing image pickup of an inside of a subject;
performing detection of a candidate area from the endoscope image;
in response to detecting the candidate area,
acquiring a position of the candidate area in the endoscope image; and generating a first display image comprising:
  a main area;
  a sub area adjacent to the main area;
  the endoscope image arranged in the main area;
  a second endoscope image, based on the endoscope image, in the main area, is further arranged in the sub area;
  a plurality of detection indicators, indicating the detection of the candidate area, arranged in the main area so as to be located at a periphery of the endoscope image to surround the endoscope image; and
  a detection position image separately arranged in the sub area, wherein a position of the detection position image in the sub area is set to correspond to the detected position of the candidate area in the endoscope image; and
in response to not detecting the candidate area, generating a second display image comprising the endoscope image arranged in the main area,
  wherein the second display image does not include the detection position image and the plurality of detection indicators,
wherein the periphery of the endoscope image comprises:
  a first periphery;
  a second periphery adjacent to the first periphery; and
  a third periphery adjacent to the second periphery, the second periphery being disposed between the first periphery and the third periphery, and
wherein in the first display image, the plurality of detection indicators comprises a first indicator at the first periphery and a second indicator at the third periphery, and no indicator of the plurality of detection indicators or another indicator is arranged in the second periphery.

32. An endoscope diagnosis support method comprising:
generating an endoscope image based on an image pickup signal output by an endoscope, the image pick up signal being obtained by the endoscope performing image pickup of an inside of a subject;
performing detection of a candidate area from the endoscope image;
in response to detecting the candidate area,
  acquire a position of the candidate area in the endoscope image; and
  generating a first display image comprising:
    a main area;
    a sub area adjacent to the main area;
    the endoscope image arranged in the main area;
    a second endoscope image, based on the endoscope image in the main area, is further arranged in the sub area
    a plurality of detection indicators, indicating the detection of the candidate area, arranged in the main area so as to be located at a periphery of the endoscope image to surround the endoscope image; and
    a detection position image separately arranged in the sub area, wherein a position of the detection position image in the sub area is set to correspond to the detected position of the candidate area in the endoscope image; and
in response to not detecting the candidate area, generating a second display image comprising the endoscope image arranged in the main area,
  wherein the second display image does not include the detection position image and the plurality of detection indicators,
wherein the periphery of the endoscope image comprises:
  a first periphery;
  a second periphery adjacent to the first periphery; and
  a third periphery adjacent to the second periphery, the second periphery being disposed between the first periphery and the third periphery, and
wherein in the first display image, the plurality of detection indicators comprises a first indicator at the first periphery and a second indicator at the third periphery, and no indicator of the plurality of detection indicators or another indicator is arranged in the second periphery.

* * * * *